United States Patent [19]

Ferris et al.

[11] 4,385,188

[45] May 24, 1983

[54] PROCESS FOR REMOVING METHANOL FROM AQUEOUS FORMALDEHYDE

[75] Inventors: Theodore V. Ferris; Richard C. Kmetz, both of Longmeadow, Mass.

[73] Assignee: Monsanto Company, St. Louis, Mo.

[21] Appl. No.: 309,960

[22] Filed: Oct. 9, 1981

[51] Int. Cl.³ .............................................. C07C 47/058
[52] U.S. Cl. ..................................... 568/493; 568/473
[58] Field of Search ................. 568/472, 493, 471, 473

[56] References Cited

U.S. PATENT DOCUMENTS 3,113,972 12/1963 Kodama et al. .................. 568/473
3,174,911 3/1965 Webb ................................. 568/473
4,119,673 10/1978 Aichs et al. ....................... 568/473

*Primary Examiner*—Werren B. Lone
*Attorney, Agent, or Firm*—R. Bruce Blance; William J. Farrington; Paul D. Matukaitis

[57] ABSTRACT

Aqueous formaldehyde solutions containing minor amounts of methanol are substantially stripped of methanol by a low energy process at relatively low temperature by means of recycled inert gas in a stripping column comprising at least about 1.5 theoretical transfer units for stripping methanol.

12 Claims, No Drawings

PROCESS FOR REMOVING METHANOL FROM AQUEOUS FORMALDEHYDE

BACKGROUND OF THE INVENTION

This invention relates to a process for removing methanol from aqueous formaldehyde solutions by stripping the solution with an inert gas.

Aqueous formaldehyde solutions which are obtained in the manufacture of formalin by oxidation of methanol, contain as much as 10 weight percent of methanol. In such solutions formaldehyde combines with water to give methylene glycol and higher polyoxymethylene glycols and with methanol to give methyl hemiformal and polyoxymethylene glycol monomethyl ethers. The chemical combination of methanol tends to suppress the formation of paraform in such aqueous formaldehyde solutions but reduces the efficiency of preparation of phenolic and amino resins prepared by the reaction of phenol and amino resin precursors with such formaldehyde solutions. The chemical combination interferes with the removal of methanol from such aqueous formaldehyde solutions.

The present invention is an improved process for removal of methanol from an aqueous formaldehyde solution by stripping the solution with an inert gas. In contrast with the high reflux ratios required in the removal of methanol by distillation, little or no reflux is required and considerable improvement in energy efficiency of the process is realized. By means of the stripping step, concentrated aqueous formaldehyde solutions of low methanol content can be readily obtained and can be used advantageously in the manufacture of phenolic and amino resins and particularly of $C_2$ and higher alkylated amino resins. Methanol contents of less than 2 weight percent are readily obtained.

The process comprises stripping methanol continuously from the aqueous formaldehyde solution with an inert gas stream by countercurrent flow in a stripping column comprising at least about 1.5 theoretical transfer units for methanol stripping. The stripping temperature and the ratio of stripping gas to aqueous formaldehyde is selected to provide a concentration of vapors of aqueous formaldehyde in the gas emerging from the stripping column of no more than about 50 mol percent. The inert gas stream can be treated to recover most of the stripped methanol, and any accompanying water and formaldehyde and can be recycled to the bottom of the stripper column to repeat the stripping process.

The inert stripping gas is any non-condensible gas which is inert to or non-reactive with the various components of the aqueous formaldehyde solution. Preferably it is a non-flammable, relatively non-toxic and relatively water-insoluble gas. Thus it is advantageously selected from the group consisting of nitrogen, helium, neon, argon and mixtures thereof.

The operation of the stripping column is dependent on several parameters including temperature of the column, ratio of stripping gas to aqueous formaldehyde solution, the number of ideal stages or theoretical transfer units in the column, and the residence time of the aqueous formaldehyde solution.

The temperature of the stripping column can be any temperature from atmospheric temperature up to the temperature at which the partial pressure of the vaporized aqueous formaldehyde under the operating conditions of the column is no more than about 50 percent of the total gas pressure of the gas leaving the top of the column or in other words the temperature at which the gas leaving the top of the column contains no more than about 50 mol percent of condensible vapors comprising formaldehyde, water and methanol. Preferably the temperature is selected so that, under the operating conditions of the column, the gas leaving the top of the column comprises about 20 to about 40 mol percent of condensible vapors. Advantageously the column is operated under conditions such that the temperature of the column is in the range of about 60° to about 85° C. and more preferably in the range of about 65° to about 80° C. Similarly the weight ratio of stripping gas to aqueous formaldehyde solution passed through the column per unit time is selected so that under the operating conditions of the column the gas mixture leaving the column contains no more than about 50 mol percent of vapors of aqueous formaldehyde and preferably contains from about 20 to about 40 mol percent. In practice, the inert gas stream in the stripping column is advantageously maintained at a pressure above about 0.5 atmospheres, preferably in the range of about 1 to about 2 atmospheres and the ratio of gas entering the stripping column to aqueous formaldehyde solution added to the stripping column is advantageously in the range of about 0.5 to about 2.5 by weight per unit time and is preferably in the range of about 1.0 to about 2.0.

In order to obtain significant removal of methanol from the aqueous formaldehyde by means of the stripping column without excessive removal of formaldehyde, the stripping column should comprise at least about 1.5 theoretical transfer units and preferably about 3 or more theoretical transfer units. The number of theoretical transfer units is determined from the following relationship:

$$NTU = \frac{P_t - P_b}{\frac{1}{2}(\Delta P_t + \Delta P_b)}$$

where

NTU = number of transfer units in the stripping column under steady state conditions, $P_t$ = vapor pressure of methanol in the gas stream emerging from the top of the stripping column, $P_b$ = vapor pressure of methanol in the gas stream entering the bottom of the stripping column, $$\Delta P_t = P_t(e) - P_t$$

$P_t(e)$ = equilibrium vapor pressure of methanol for the aqueous formaldehyde/methanol solution at the top of the column, at the temperature at the top of the column, $$\Delta P_b = P_b(e) - P_b$$

$P_b(e)$ = equilibrium vapor pressure of methanol for the aqueous formaldehyde/methanol solution at the bottom of the column, at the temperature at the bottom of the column.

The equilibrium vapor pressures are determined from standard vapor liquid equilibrium data, for example they may be obtained from data stored in the data base sold by Monsanto under the registered trademark Flowtran.

In aqueous formaldehyde solutions a methanol-methyl hemiformal-polyoxymethylene glycol monomethyl ether equilibrium exists and favors the hemiformals. The equilibrium can be displaced towards methanol by raising the temperature and by dilution of the formaldehyde solution with water. Methanol can be readily removed from dilute aqueous formaldehyde solutions by fractional distillation. However with concentrated solutions of aqueous formaldehyde which are gaining commercial favor, wherein the formaldehyde concentration is above about 40 weight percent and particularly wherein the formaldehyde concentration is above about 50 weight percent, processes to remove methanol and in particular the stripping process of the present invention to remove methanol at the relatively low temperatures used with the purpose of conserving energy, is more difficult because most of the methanol is chemically combined as hemiformals at these temperatures and, although reversal of the methanol hemiformal reaction occurs progressively with the removal of methanol from the solutions, the rate of reversal is rather low. Efficient removal of methanol in a stripping column comprising conventional packaging or tray columns would require an excessively high column. It is therefore advantageous to increase the residence time of the aqueous formaldehyde in the stripping column by any convenient means to allow equilibrium reversal of the methanol hemiformal reaction to occur. Preferably residence zones are introduced to allow the aqueous formaldehyde solution to remain quiescent out of contact with the stripping gas generally for at least about 4 minutes until a significant concentration of free methanol has been established. The column then becomes a series of stripping zones separated by residence zones, with the free methanol being generated be reversal of the methanol hemiformal reaction in the residence zones. One way to obtain quiescent residence zones is by introduction into the column of a number of chimney trays which are essentially overflow liquid trays with gas chimneys to allow the stripping gas ascending to pass by the aqueous formaldehyde solution held in the chimney trays. Another way is by means of circulation loops placed at intervals along the stripping column, the loops being equipped with reservoirs of suitable size to isolate the formaldehyde solution from the gas stream for the desired time. Thus with stripping columns comprising conventional packing or trays such as sieve trays, glass trays, bubblecap trays or valve trays to provide intimate contact between the aqueous formaldehyde solution and the stripping gas for efficient extraction of methanol by the gas stream, it is advantageous to include residence zones at intervals in the column to reduce the height of the column required for efficient stripping of methanol. For example a 30 meter stripping column capable of handling about 5 metric tons of formalin product per hour, provides about four theoretical transfer units determined by means of the relationship set forth above, for the stripping of methanol when it is packed with 21 meters of Pall ring packing divided into 5 zones with each zone separated with a chimney tray of 10 cm. depth, providing a residence time of about 6 minutes in each residence tray. Similarly a 30 meter stripping column containing 45 sieve trays can provide about four theoretical transfer units when 4 residence trays each providing a residence time of about 6 minutes are placed at intervals along the column. Thus by means of the residence zones, transfer units of height in the range of about 1 to about 10 meters are readily obtained and allow the desired weight ratio of gas to liquid passing through the stripping column per unit time to be achieved.

The inert stripping gas which emerges from the stripping column contains methanol, formaldehyde and water vapors. The gas is advantageously treated to remove the condensible components for example by scrubbing the gas with water or with aqueous formaldehyde.

Optionally the stripping gas which emerges from the stripping column can be passed to a partial condenser and the condensate can be returned to the top of the stripping column. In this manner, most of the formaldehyde and water is condensed and returned as a reflux to the stripping column while the inert gas stream retains most of the methanol removed from the aqueous formaldehyde solution in the stripping column. When the aqueous formaldehyde condensate is refluxed to the stripping column in this manner, the stripping column can advantageously be equipped with a top stage comprising a contact zone for intimate contact between the ascending inert gas stream and the descending aqueous formaldehyde reflux and a residence zone above the entry port for the initial aqueous formaldehyde solution entering the stripping column from the absorption train. The inert gas stream emerging from the partial condenser is then passed through a condenser and a condensate comprising a substantial amount of methanol is obtained.

In comparison with a fractional distillation column for removal of methanol from an aqueous formaldehyde solution, the gas-stripping process of the present invention can reduce the energy requirement for methanol removal by about 50 percent or more without sacrifice in separating efficiency. Advantageously for a balance in energy savings and separating efficiency, the stripping column is maintained at a temperature in the range of about 60° to about 85° C., and more preferably in the range of about 65° to about 80° C. and the ratio of stripping gas fed into the bottom of the stripping column to the aqueous formaldehyde solution fed to the stripping column is in the range of about 0.5 to about 2.5 by weight per unit of time and more preferably in the range of about 1.0 to about 2.0.

Since the stripping column is operated at a relatively low temperature and since the reflux, if any, returned to the stripping column is a very minor fraction of the total amount of aqueous formaldehyde solution in the stripping column, the heat required to maintain the stripping column at the operating temperature is substantially less than the heat required for a distillation column.

The formaldehyde solution obtained by the process of the invention, is a disinfectant, tanning agent, reducing agent and a starting material for the manufacture of organic chemicals and synthetic resins and adhesives.

The invention is further illustrated but is not intended to be limited by the following examples in which parts and percentages are by weight unless specified otherwise.

EXAMPLE 1

A 6.1 m stainless steel steam-traced insulated column of 16.1 cm internal diameter is packed with five beds of 1.27 cm chemically resistant porcelain saddles sold by the Norton Company under the tradename Intalox, the beds being separated from each other by residence trays of 1.90 liter capacity. The column contains 1.8 transfer units. To the top of the column 41.4 kg per hour of an aqueous formaldehyde solution comprising 36.9 weight percent formaldehyde, 4.2 weight percent methanol and 58.9 weight percent water is fed at a temperature of 68°

C. A stream of heated nitrogen at a temperature of 162° C. is passed into the bottom of the column at a rate of 81.8 pounds per hour and is allowed to flow countercurrent to the descending aqueous formaldehyde solution. The temperature of the column is maintained at 71° C. at the top and 70° C. at the bottom. The composition of the aqueous formaldehyde solution product drawn from the column sump is 49.3 weight percent formaldehyde, 1.47 weight percent methanol and 49.3 weight percent of water. The ratio of formaldehyde to methanol increased from 8.82 to 33.5 by the stripping process. The steam consumption is 21 kg./hr. Methanol removal is 83%.

EXAMPLE 2

An aqueous formaldehyde solution comprising 31.0 weight percent formaldehyde, 6.1 weight percent methanol and 62.9 weight percent water, at a temperature of 60° C. is fed to the top of the stripping column of example 1, at a rate of 42.2 kg per hour and is allowed to pass countercurrent to a stream of nitrogen introduced to the bottom of the column at a temperature of 162° C. and at a rate of 61.3 kg per hour. The column is maintained at a temperature ranging from 67° C. at the top to 66° C. at the bottom. The composition of the aqueous formaldehyde solution drawn from the sump is 33.8 weight percent formaldehyde, 3.4 weight percent methanol, and 62.8 weight percent water. The ratio of formaldehyde to methanol is increased from 5.1 to 10.0 by the stripping process. The steam consumption is 10.5 kg./hr. Methanol removal is 79%.

EXAMPLE 3

An aqueous formaldehyde solution comprising 44 weight percent formaldehyde, 5.8 weight percent methanol and 50.2 weight percent water, at a temperature of 66° C. is fed to the top of the stripping column of example 1, at a rate of 40.9 kg. per hour, and is allowed to pass countercurrent to a stream of nitrogen containing condensibles (0.36 mol% formaldehyde, 0.06 mol% methanol, 1.29 mol% water, and 98.29 mol% nitrogen), at a temperature of 162° C., and flowing at a rate of 55.7 kg. per hour. The column is maintained at a temperature ranging from 75° C. at the top to 72° C. at the bottom. The composition of the aqueous formaldehyde product drawn from the sump is 63.33 weight percent formaldehyde, 2.10 weight percent methanol, and 34.57 weight percent water. The methanol removal is 81%. The steam consumption is 25.6 kg. per hour.

EXAMPLE 4

An aqueous formaldehyde solution comprising 43.6 weight percent formaldehyde, 4.4 weight percent methanol, and 52 weight percent water, at a temperature of 63° C. is fed to the residence tray immediately above the middle bed of the stripping column of example 1, at a rate of 41 kg. per hour, and is allowed to pass countercurrent to a stream of nitrogen containing condensibles (0.05 mol% formaldehyde, 0.24 mol% methanol, 1.41 mol% water, and 98.29 mol% nitrogen), at a temperature of 164° C., and flowing at a rate of 55.7 kg. per hour. At the same time, the exit gas stream leaving the top of the column enters an atmospheric shell and tube condenser from which a condensed reflux solution, comprising 19.5 weight percent formaldehyde, 5.9 weight percent methanol and 74.6 weight percent water, is fed back to the top of the column after being reheated to 80° C., at a rate of 10.9 kg. per hour. The column is maintained at a temperature ranging from 75° C. at the top to 69° C. at the bottom. The composition of the aqueous formaldehyde product drawn from the sump is 48.67 weight percent formaldehyde, 2.92 weight percent methanol, and 48.41 weight percent water. Steam consumption is 27 kg. per hour. Methanol removal is 41%.

EXAMPLE 5

The stripper column 27.7 meters high is packed with 21 meter of Pall ring packing in 5 zones, the zones being separated by chimney trays of 10 cm. depth. Per hour an aqueous formaldehyde solution containing 8131 parts of formaldehyde, 653 parts of methanol and 8184 parts of water at a temperature of 84° C. is introduced continuously into the stripper column above the 5th stage and passed downward in the stripping column. Per hour 13742 parts of stripping gas comprising 12290 parts of nitrogen, 3.8 parts of formaldehyde, 28.3 parts of methanol, 134 parts of water, 259 parts of hydrogen and 1026 parts of carbon dioxide is introduced to the bottom of the stripping column and passed upward through the column. The temperature of the stripping column is 77° C. at the bottom and 73° C. at the top. The gas stream emerging from the stripper column comprises 1333 parts of formaldehyde, 714 parts of methanol, 3631 parts of water, 12300 parts of nitrogen, 259 parts of hydrogen and 1030 parts of carbon dioxide. The gas stream is passed to a partial condenser and the partial condensate comprising 1027 parts of formaldehyde, 263 parts of methanol and 2445 parts of water is returned to the top section of the stripping column. The gas stream emerging from the partial condenser is then passed through a precondenser and countercurrent in a final condenser to a circulated aqueous stream made up with 2000 parts of water per hour. An aqueous formaldehyde solution containing 307 parts of formaldehyde, 426 parts of methanol, and 2624 parts of water is collected in a distillate receiver. 15328 parts of aqueous formaldehyde solution containing 7829 parts of formaldehyde, 230 parts of methanol, 7132 parts of water and 137 parts dissolved gases is drawn off from the bottom of the stripping column. The methanol content is 1.5 percent. The energy requirement for the stripping column is 0.75 gigajoule per metric ton of product. Methanol removal is 65%.

What is claimed is:

1. A process for stripping methanol from aqueous formaldehyde solution with a counter-current inert gas stream in a stripping column comprising at least about 1.5 theoretical transfer units for methanol stripping, the stripping being carried out at a temperature and at a ratio of stripping gas to aqueous formaldehyde to provide a concentration of condensible vapors in the gas emerging from the stripping column of no more than about 50 mol percent.

2. The process of claim 1 wherein the stripping column comprises at least about three theoretical transfer units.

3. The process of claim 1 or 2 wherein the height of the theoretical transfer unit is in the range of about 1 to about 10 meters.

4. The process of claim 3 wherein the temperature of the stripping column is in the range of about 60° to about 85° C.

5. The process of claim 3 wherein the stripping column contains residence zones providing average residence times of at least about 4 minutes per zone.

6. The process of claim 5 wherein the residence zones are chimney trays.

7. The process of claim 5 wherein the residence zones are circulation side loops and reservoirs.

8. The process of claim 3 wherein the insert gas is selected from the group consisting of nitrogen, helium, neon and argon.

9. The process of claim 3 wherein the weight ratio of inert gas to aqueous formaldehyde flowing through the stripping column per unit time is in the range of about 0.5 to about 2.5.

10. The process of claim 3 wherein the weight ratio of inert gas to aqueous formaldehyde flowing through the stripping column per unit time is in the range of about 1.0 to about 2.0.

11. The process of claim 10 wherein the stripping gas which emerges from the stripping column is passed through a partial condenser, and the condensed aqueous formaldehyde solution which forms is refluxed to the stripping column.

12. The process of claim 11 wherein the stripping gas which emerges from the partial condenser is passed through a condenser to substantially remove methanol and the remaining condensible vapors and the gas is recycled through the stripping column.

* * * * *